US012580058B2

(12) United States Patent
Guttikonda et al.

(10) Patent No.: US 12,580,058 B2
(45) Date of Patent: Mar. 17, 2026

(54) PREDICTING PERSISTENCE OR REDUCTION IN USER INTERACTIONS ACROSS SESSIONS USING MACHINE LEARNING MODELS AND EVENT DATA

(71) Applicant: Click Therapeutics, Inc., New York, NY (US)

(72) Inventors: Sudheer Guttikonda, Edison, NJ (US); Gunther Havel, Portsmouth, NH (US); William Morse, New York, NY (US); Daniel Rimm, New York, NY (US)

(73) Assignee: Click Therapeutics, Inc., New York, NY (US)

( * ) Notice: Subject to any disclaimer, the term of this patent is extended or adjusted under 35 U.S.C. 154(b) by 0 days.

(21) Appl. No.: 18/625,009

(22) Filed: Apr. 2, 2024

(65) Prior Publication Data

US 2025/0308659 A1     Oct. 2, 2025

(51) Int. Cl.
| | |
|---|---|
| *G16H 20/00* | (2018.01) |
| *G16H 80/00* | (2018.01) |
| *H04L 67/50* | (2022.01) |

(52) U.S. Cl.
CPC .............. *G16H 20/00* (2018.01); *G16H 80/00* (2018.01); *H04L 67/535* (2022.05)

(58) Field of Classification Search
None
See application file for complete search history.

(56) References Cited

U.S. PATENT DOCUMENTS

| | | | |
|---|---|---|---|
| 11,307,892 B2 * | 4/2022 | Kelly | .................... G06N 20/00 |
| 2018/0096111 A1 | 4/2018 | Wells et al. | |

OTHER PUBLICATIONS

Kelders et al. J Med Internet Res 2012;14(6):e152; 24 pages (Year: 2012).*
Kumar et al. Am J Prev Med 2013; 45(2):228-236. (Year: 2013).*
Michie et al. J Med Internet Res 2017 vol. 19(6); e232; 13 pages. (Year: 2017).*
Hart ("Machine Learning 101: The What, Why and How of Weighting" in KDnuggets date Nov. 26, 2019; 12 pages and retrieved online at https://www.kdnuggets.com/tag/machine-learning/page/6).*
Ekpezu et al. (JMIR AI vol. 2; 12 pages) (Year: 2023).*
Extended European Search Report on EP Appl. No. 24176094.1 dated Nov. 5, 2024.

* cited by examiner

*Primary Examiner* — Lori A. Clow
(74) *Attorney, Agent, or Firm* — MORRISON & FOERSTER LLP

(57)     ABSTRACT

Provided herein are systems and methods for methods for detecting expected reductions of interactions across sessions. A computing system can identify event data identifying interactions by a user with a first session for digital therapeutic content to address a condition. The computing system can apply the event data to a machine learning (ML) model. The computing system can generate a likelihood of the user interacting with a second session for digital therapeutic content based on applying the event data to the ML model. The computing system can detect an expected reduction in interactions by the user with the second session, responsive to the likelihood of the user not satisfying a threshold. The computing system can provide an output for the user based on detecting the expected reduction in interactions. In this manner, the efficacy of the medication that user is concurrently taking to address the condition may be improved.

20 Claims, 6 Drawing Sheets

PREDICTING PERSISTENCE OR REDUCTION IN USER INTERACTIONS ACROSS SESSIONS USING MACHINE LEARNING MODELS AND EVENT DATA

BACKGROUND

In a session, a computing device and a remote server may communicate data associated with user interactions detected via a user interface. For example, a digital therapeutics application running on the computing device may receive data from the remote server to present digital therapeutic content via the user interface (e.g., in the form of audio, visual, or text content). Digital therapeutics may include evidence-based therapeutic interventions delivered directly to the user via the application on the computing device. The digital therapeutic content presented on the user interface may prompt the user to perform an activity triggering certain portions of the user's neural system in furtherance of addressing a condition. Each time a user interaction is detected on one of the user interface elements, the computing device may generate the data based on the user interaction to transmit via a network. A remote server hosting resources for the application may in turn return response data to the computing device.

The sessions may involve various processing operations on both the computing device and the remote server, such as processing the user interactions to invoke functions, rendering the user interface elements, and communicating the data, among others. Depending on the complexity of the processing operations and the rate of user's interactions with the user interface elements, the amount of processing power, the memory, and network bandwidth consumed may be significant. There may be a number of technical challenges with predicting user interactions in connection with allocating computing resources. For one, users may not be uniform in how they behave, such that a particular user may exhibit diverse behavior from another user, making it difficult to treat all users in the same manner. For another, interaction data may be sparse, especially for new users of the application, and insufficient to make accurate predictions. In addition, the scalability of predicting user interactions with a multitude of users and user interface elements may be also challenging.

The inability of accurately and precisely predicting user interactions may result in inefficient allocation of resources (e.g., computational power and network bandwidth) from delivering data for presentation of content and interactivity through the user interface elements. The inaccurate predictions may lead to selection of content that does not result in user interactions, thereby wasting computing resources and also lowering the quality of human-computer interactions (HCI) between the user and the user interface. Furthermore, there may be a negative feedback loop for the predictive analytics as a result of the provision of such content and interactivity and collection of poor-quality user interaction data.

In the context of digital therapeutics, for the user to receive the full ameliorative effects, the user should interact with the user interface to perform activities as directed by the digital therapeutic content aimed at addressing the condition. Lack of adherence as exhibited by low or no interaction with the user interfaces can significantly impact an outcome of the user with respect to the digital therapeutic. The rate of drop off may significantly increase as the user progresses through the treatment. When the user fails to engage actively, it can hinder progress and prolong the healing process of the conditions of the user. One consequence to the user as a result of non-interaction with the digital therapeutic may be the potential stagnation or worsening of the user's condition. The delivery of ineffective digital therapeutic content may also result in the inefficient allocation of resources (e.g., computational power and network bandwidth) as well as decreased quality of HCI.

SUMMARY

To address these and other technical challenges, the digital therapeutics application can use certain event data from prior sessions and a machine learning (ML) model to predict likelihoods of the user interacting with subsequent sessions provided to the user. There are several technical advantages and benefits with the ability to predict the likelihoods of a user interacting in subsequent sessions. For one, the prediction may be used to determine whether to continue with the digital therapy sessions or to provide targeted countermeasures aimed at improving user adherence to the therapy regimen. This may allow the computing system to better and more efficiently allocate computing resources and network bandwidth in carrying out operations to provide further digital therapeutics or countermeasures.

For another, with the improvement in treatment adherence, the user may be able to receive the full benefits and effects of the digital therapeutic in remedying, alleviating, or otherwise addressing the user's medical condition. Therefore, computing resources consumed in delivering digital therapeutic content to which the user would not have responded to may be conserved. In addition, since the computing system may alert the healthcare provider or the administrator of the digital therapeutic when the user is predicted to drop off, the provider (or support members) may be able to identify which users to manually intervene (e.g., by contacting the user). For example, a signal may be output that indicates that a user is predicted to drop off, which may be used to indicate to the provider that an intervention is required. The in-person intervention may not only improve the effectiveness of the digital therapeutic delivered to the user but also any medications that the user may be on in concurrence with the digital therapy regimen.

To that end, the computing system may present a digital therapeutic content via the user interface to direct the user to perform an activity. The activity may be in accordance with a particular task, such as an implicit association task (IAT), attention bias modification training (ABMT), emotional faces memory task (EFMT), digital support tool (DST), and adaptive goal setting (AGS), among others. During the session, the computing system may monitor event data of interactions during a session for providing digital therapeutic content to address a condition. The event data may include various information related to the interactions and contextual factors, such as an identification of the content provided, activity duration, a metric indicating a number or rate of interactions, a metric related to the activity, task, or the condition, a number of prior drop offs, and an indication of whether the user contacted a support center, among others.

The computing system may apply the event data to the model to determine a likelihood that the user will interact with the digital therapeutic content in a subsequent session. The subsequent session may correspond to the digital therapeutic content to be provided in the next time period (e.g., hour, day, or week) to the user. The model may have been initialized, trained, and established using training data formed from prior sessions or prior users with similar profiles (e.g., the same conditions) or other factors. The training data may include a user's historical interactions from one session and activity performance in subsequent sessions. From the training data, the model may learn to predict likelihood of user interactions in the follow-on sessions. The model may indicate that certain factors in the event data, such as recent drop offs or use of the digital therapeutic application in the previous day, may be more predictive of future drop offs than other parameters.

The computing system may compare the likelihood with a threshold to determine whether the user is expected to drop off or continue with the digital therapeutics sessions. When the likelihood exceeds the threshold, the computing system may predict that the user will persist in interactions for the subsequent session. The computing system may also continue with the subsequent session as previously defined. On the other hand, when the likelihood does not exceed the threshold, the computing system may predict a reduction in user interaction for the subsequent session.

The computing system may select a countermeasure to handle the expected reduction in interactions. The countermeasures may include, for example, a pre-generated notification to the user to encourage engagement, a notification to the support center that the user is about to drop off, triggering a generative artificial intelligence (AI) model to create a custom notification, or a modification of the digital therapeutic content, among others. The computing system may provide the selected countermeasure as output to the application or the support center. When the likelihood indicates a low-risk of drop off in in the subsequent session, the computing system may select and provide a notification to the user or support center to indicate that the user is at low-risk of dropping off. When the likelihood indicates a high-risk in the user dropping off in the subsequent session, the computing may select and provide additional support and intervention to increase the adherence of the user.

By using the ML model to predict a likelihood of the user interacting in subsequent sessions based on event data from prior sessions, the application may be able to determine whether to continue with the session or provide measures to counter potential reductions in user interactions. The reliance on prior event data from the user and other users may resolve the issue with scarcity of data as well as type of event data (e.g., information on user interactions and related contextual factors) in accurately and precisely predicting user interactions. The accurate predictions may allow the application to efficiently allocate computing resources (e.g., computational power and network bandwidth) in determining whether to continue with digital therapeutic content or provide countermeasures.

As a result of providing targeted countermeasures when the user is expected to drop off, the application may increase adherence of the user with the digital therapeutic provided through the sessions. This may further reduce wasted computing resources that would have otherwise been consumed in providing a session that the user will not interact with. The increased adherence may also improve the quality of HCI between the user and the application, as well as more effectively treat, ameliorate, or otherwise address the user's condition. The provision of digital therapeutics through the application in this manner may be used to increase the efficacy of the medications that the user may be on to address the condition.

Aspects of the present disclosure are directed to systems and methods for detecting expected reductions of interactions across sessions. One or more processors coupled with memory can identify event data identifying interactions by a user with a first session for digital therapeutic content to address a condition. The one or more processors can apply the event data to a machine learning (ML) model. The ML model may be trained using a plurality of examples. Each of the plurality of examples may include (i) a respective event data identifying interactions by a corresponding user with a respective session for digital therapeutic content and (ii) a respective identification of whether the corresponding user interacted with a subsequent session after the respective session. The one or more processors can generate a likelihood of the user interacting with a second session for digital therapeutic content to address the condition subsequent to the first session based on applying the event data to the ML model. The one or more processors can detect an expected reduction in interactions by the user with the second session, responsive to the likelihood of the user not satisfying a threshold. The one or more processors can provide an output for the user based on detecting the expected reduction in interactions.

In some embodiments, the one or more processors can generate a likelihood of a second user interacting with a fourth session subsequent to a third session for the second user, based on applying event data identifying interactions by the second user with the third session to the ML model. In some embodiments, the one or more processors can detect an expected persistence in interactions by the second user with the fourth session, responsive to the likelihood of the second user satisfying the threshold. In some embodiments, the one or more processors can provide an output for the second user based on detecting the expected persistence in interactions.

In some embodiments, the one or more processors can transmit the output comprising a notification to a computing device of a support center, the computing device configured to initiate communications with the user subsequent to receipt of the notification. In some embodiments, the one or more processors can select the output from a plurality of candidate outputs based on the likelihood of the user interacting with the second session, the plurality of candidate outputs comprising at least one of: (i) a first candidate output indicating to a computing device to initiate communications via at least one of phone, email, or in-app chat or (ii) a second candidate output indicating to the computing device to monitor subsequent interactions by the user.

In some embodiments, the one or more processors can transmit the output comprising a predefined notification to direct the user to interact with the second session to be provided to the user. In some embodiments, the one or more processors can identify profile information associated with the user, responsive to detecting the expected reduction in interactions by the user. In some embodiments, the one or more processors can apply the profile information to a generative transformer model to generate a notification to direct the user to interact with the second session to be provided to the user. In some embodiments, the one or more processors can provide the notification to direct the user to interact with the second session to be provided to the user.

In some embodiments, the one or more processors can modify, the digital therapeutic content to be presented in the second session based on detecting the expected reduction in interactions, and wherein providing the output further comprises providing the second session for the modified digital therapeutic content to the user. In some embodiments, the one or more processors can identify second event data identifying interactions by the user with the second session for digital therapeutic content to address the condition. In some embodiments, the one or more processors can apply the second event data to a machine learning (ML) model to generate a likelihood of the user interacting with a third session for digital therapeutic content to address the condition subsequent to the second session.

In some embodiments, the one or more processors can determine whether a change in responsiveness occurs in the user based on a comparison of the likelihood of the user interacting with the second session and the likelihood of the user interacting with the third session. The event data further comprises at least one of: (i) an identifier of the digital therapeutic content provided in the first session, (ii) a time during which the first session is provided, (iii) a sequence identifier of the first session within a plurality of sessions, (iv) a metric indicating a degree of interactions in the first session, (v) an indication of whether the user contacted a computing device for support, (vi) a type of a user device associated with the user, (vii) a number of prior expected reductions, (ix) a metric associated with a task performed in the first session, or (x) a metric associated with the condition. The user is on a medication to address the condition, in at least partial concurrence with at least one of the first session or the second session.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following enumeration of the sections of the specification and their respective contents may be helpful:

Section A describes systems and methods for detecting expected reductions or persistence of interactions across sessions; and Section B describes a network and computing environment which may be useful for practicing embodiments described herein.

Figure 1:
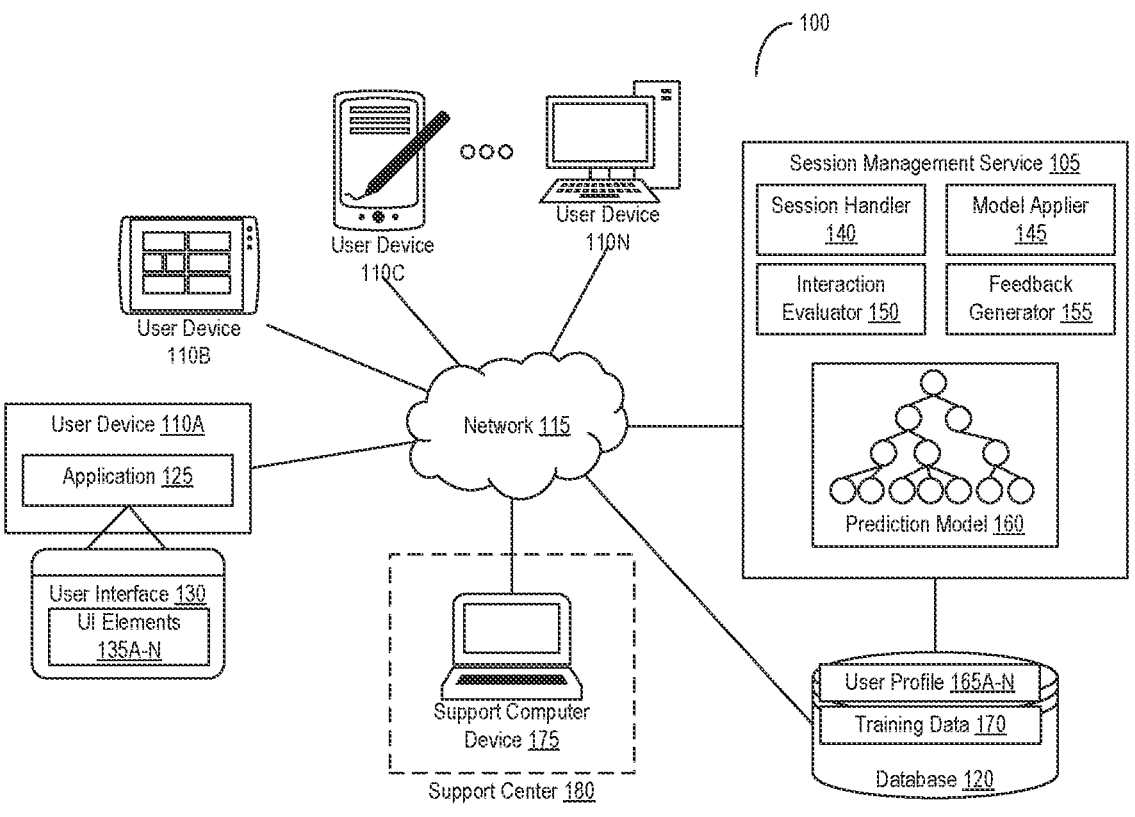
FIG. 1 depicts a block diagram of a system for detecting expected reductions or persistence of interactions across sessions, in accordance with an illustrative embodiment.

A. Systems and Methods for Detecting Expected Reductions or Persistence of Interactions Across Sessions Referring now to FIG. 1, depicted is a block diagram of a system 100 for detecting expected reductions or persistence of interactions across sessions. In an overview, the system 100 may include at least one session management service 105, a set of user devices 110A-N (hereinafter generally referred to as user devices 110), and a support center 180 with at least one support computer device 175, communicatively coupled with one another via at least one network 115. At least one of the user devices 110 (e.g., the first user device 110A as depicted) may include at least one application 125. The application 125 may include or provide at least one user interface 130 with one or more user interface (UI) elements 135A-N (hereinafter generally referred to as UI elements 135). The session management service 105 may include at least one session handler 140, at least one model applier 145, at least one interaction evaluator 150, at least one feedback generator 155, and at least one prediction model 160, among others. The session management service 105 may include or have access to at least one database 120. The database 120 may store, maintain, or otherwise include one or more user profiles 165A-N (hereinafter generally referred to as user profiles 165) and training data 170. The functionalities of the application 125 on the user device 110 may be performed in part on the session management service 105, and vice-versa. Each of the components of the system 100 can be implemented using the computing system as described in Section B.

In further detail, the session management service 105 (sometimes herein generally referred to as a messaging service) may be any computing device comprising one or more processors coupled with memory and software and capable of performing the various processes and tasks described herein. The session management service 105 may be in communication with the one or more user devices 110 and the database 120 via the network 115. The session management service 105 may be situated, located, or otherwise associated with at least one computer system. The computer system may correspond to a data center, a branch office, or a site at which one or more computers corresponding to the session management service 105 are situated.

Within the session management service 105, the session handler 140 can manage a session and receive interactions from a user. The interaction evaluator 150 can detect interactions with the application 125. The model applier 145 can use the prediction model 160 to determine a likelihood of the user interacting with a subsequent session. The feedback generator 155 can generate an output based on the likelihood of interaction to have the user interact with the digital therapeutic application. The prediction model 160 can include any machine learning model to determine likelihoods of users interacting in subsequent sessions.

The architecture for the machine learning model of the prediction model 160 can include, for example, a deep learning neural network (e.g., convolutional neural model architecture), a regression model (e.g., linear or logistic regression model), a random forest, a support vector machine (SVM), a clustering algorithm (e.g., k-nearest neighbors), or a Naïve Bayesian model, among others. In general, the prediction model 160 may have at least one input and one output. The input and output may be related via a set of weights. The input may include event data from at least one previous session. The output may include a likelihood of the user interacting in at least one subsequent sessions. The set of weights can be in accordance with the machine learning architecture. The machine learning model of the prediction model 160 can be trained using the training data 170 (e.g., in accordance with supervised learning).

The user device 110 (sometimes herein referred to as an end user computing device) may be any computing device comprising one or more processors coupled with memory and software and capable of performing the various processes and tasks described herein. The user device 110 may be in communication with the session management service 105 and the database 120 via the network 115. The user device 110 may be a smartphone, other mobile phone, tablet computer, wearable computing device (e.g., smart watch, eyeglasses), or laptop computer. The user device 110 may be used to access the application 125. In some embodiments, the application 125 may be downloaded and installed on the user device 110 (e.g., via a digital distribution platform). In some embodiments, the application 125 may be a web application with resources accessible via the network 115.

The application 125 executing on the user device 110 may be a digital therapeutics application. The application 125 may present or provide a session (sometimes referred to herein as a therapy session) to address at least one condition in the user. The condition of the end user may include, for example, chronic pain (e.g., associated with or including arthritis, migraine, fibromyalgia, back pain, Lyme disease, endometriosis, repetitive stress injuries, irritable bowel syndrome, inflammatory bowel disease, and cancer pain), a skin pathology (e.g., atopic dermatitis, psoriasis, dermatillomania, and eczema), a cognitive impairment (e.g., mild cognitive impairment (MCI), Alzheimer's, multiple sclerosis, and schizophrenia), a mental health condition (e.g., an affective disorder, bipolar disorder, obsessive-compulsive disorder, borderline personality disorder, and attention deficit/hyperactivity disorder), a substance use disorder (e.g., opioid use disorder, alcohol use disorder, tobacco use disorder, or hallucinogen disorder), and other conditions (e.g., narcolepsy and oncology or cancer), among others.

The end user may be on a medication to address the condition, in at least partial concurrence with the use of the application 125 (e.g., for any number of sessions). For instance, if the medication is for pain, the end user may be taking acetaminophen, a nonsteroidal anti-inflammatory composition, an antidepressant, an anticonvulsant, or other composition, among others. For skin pathologies, the end user may be taking a steroid, antihistamine, or topic antiseptic, among others. For cognitive impairments, the end user may be taking cholinesterase inhibitors or memantine, among others. For narcolepsy, the end user may be taking a stimulant or antidepressant, among others. The end user may also participate in other psychotherapies for these conditions. In some embodiments, the digital therapeutic content may be provided to the end user within the digital therapeutics application towards achieving an endpoint of the end user. An endpoint can be, for example, a physical or mental goal of an end user, a completion of a medication regimen, or an endpoint indicated by a doctor or an end user. At least one of the end user devices 110 may have a digital therapeutics application and may provide a session (sometimes referred to herein as a therapy session) to address at least one condition of the end user.

The application 125 can include, present, or otherwise provide at least one user interface 130 including the one or more user interface elements 135A-N (hereinafter generally referred to as UI elements 135) to a user of the user device 110. The user interface 130 may be provided in accordance with a configuration on the application 125. The UI elements 135 may correspond to visual components of the user interface 130, such as a command button, a text box, a check box, a radio button, a menu item, and a slider, among others. In some embodiments, the application 125 may be a digital therapeutics application and may provide a session (sometimes referred to herein as a therapy session) via the user interface 130 to address the condition. The user interface 130 may include the set of UI elements 135 to present digital therapeutic content.

The digital therapeutic content may be in any modality, such as text, image, audio, video, or multimedia content, among others, or any combination thereof. The content items can be stored and maintained in the database 120 using one or more files. For instance, for text, the digital therapeutic content can be stored as text files (TXT), rich text files (RTF), extensible markup language (XML), and hypertext markup language (HTML), among others. For an image, the digital therapeutic content may be stored as a joint photographic experts' group (JPEG) format, a portable network graphics (PNG) format, a graphics interchange format (GIF), or scalable vector graphics (SVG) format, among others. For audio, the digital therapeutic content can be stored as a waveform audio file (WAV), motion pictures expert group formats (e.g., MP3 and MP4), and Ogg Vorbis (OGG) format, among others. For video, the digital therapeutic content can be stored as a motion pictures expert group formats (e.g., MP3 and MP4), QuickTime movie (MOV), and Windows Movie Video (WMV), among others. For multimedia content, the digital therapeutic content can be an audio video interleave (AVI), motion pictures expert group formats (e.g., MP3 and MP4), QuickTime movie (MOV), and Windows Movie Video (WMV), among others.

The digital therapeutic content may include a set of stimuli (e.g., in the form of audio, visual, or text) for the user to carry out a particular task. The task may include, for example, an implicit association task (IAT) (e.g., associating stimuli with concepts); an attention bias modification training (ABMT) (e.g., training users to shift attention away from certain stimuli); an emotional faces memory task (EFMT) (e.g., testing users to recognize and remember certain facial emotions); digital support tool (DST) (e.g., providing messages based on expected state of user); and adaptive goal setting (AGS) (e.g., providing messages based on dynamic objectives for user); among others.

In some embodiments, the IAT of the digital therapeutic content may be the IAT as described in U.S. patent application Ser. No. 18/111,084 (published as U.S. Pat. App. Pub. No. 2023/0268037), incorporated herein by reference in its entirety. The ABMT of the digital therapeutic content may be the ABMT as described in U.S. patent application Ser. No. 18/237,567 (published as U.S. Pat. App. Pub. No. 2024/0071602), incorporated herein by reference in its entirety. In some embodiments, the EFMT of the digital therapeutic content may be the EFMT as described in U.S. Pat. No. 10,123,737, incorporated herein by reference in its entirety. In some embodiments, the DST of the digital therapeutic content may be the DST as described in U.S. patent application Ser. No. 18/130,813 (published as U.S. Pat. App. Pub. No. 2023/0360773), incorporated herein by reference in its entirety. In some embodiments, the AGS of the digital therapeutic content may be the AGS as described in U.S. patent application Ser. No. 18/208,067 (published as U.S. Pat. App. Pub. No. 2023/0410967), incorporated herein by reference in its entirety.

The database 120 may store and maintain various resources and data associated with the session management service 105 and the application 125. The database 120 may include a database management system (DBMS) to arrange and organize the data maintained thereon, such as the user profiles 165, and training data 170, among others. The database 120 may be in communication with the session management service 105 and the one or more user devices 110 via the network 115. While running various operations, the session management service 105 and the application 125 may access the database 120 to retrieve identified data therefrom. The session management service 105 and the application 125 may also write data onto the database 120 from running such operations.

On the database 120, each user profile 165 (sometimes herein referred to as a user account, user information, or subject profile) can store and maintain information related to a user of the application 125 through user device 110. Each user profile 165 may be associated with or correspond to a respective user of the application 125. The user profile 165 may identify various information about the user, such as a user identifier, the condition to be addressed, information on sessions conducted by the user (e.g., activities or lessons completed), message preferences, user trait information, and a state of progress (e.g., completion of endpoints) in addressing the condition, among others. The information on a session may include various parameters of previous sessions performed by the user and may be initially null. The message preferences can include treatment preferences and user input preferences, such as types of messages or timing of messages preferred. The message preferences can also include preferences determined by the session management service 105, such as a type of message the user may respond to. The progress may initially be set to a start value (e.g., null or "0") and may correspond to alleviation, relief, or treatment of the condition. The user profile 165 may be continuously updated by the application 125 and the session management service 105.

In some embodiments, the user profile 165 may identify or include information on a treatment regimen undertaken by the user, such as a type of treatment (e.g., therapy, pharmaceutical, or psychotherapy), a duration (e.g., days, weeks, months, or years), and a frequency (e.g., daily, weekly, quarterly, annually), among others. The user profile 165 can include at least one activity log of messages provided to the user, interactions by the user identifying performance of the specific user, and responses from the user device 110 associated with the user, among others. The user profile 165 may be stored and maintained in the database 120 using one or more files (e.g., extensible markup language (XML), comma-separated values (CSV) delimited text files, or a structured query language (SQL) file). The user profile 165 may be iteratively updated as the user performs additional sessions or responds to additional messages.

The support center 180 may correspond to a remote service, including the support computer device 175 comprising one or more processors coupled with memory and software and capable of performing the various processes and tasks described herein. The support center 180 and the support computer device 175 may be associated with an entity, such as a health care provider (e.g., clinician or staff) or an administrator of the digital therapeutic (e.g., an administrator of the session management service 105). For example, the support center 180 may be a centralized hub within an organization that may provide assistance, guidance, or direction to end users using the application 125. The support center 180 may include the support computer device 175 to use various communication channels, via the network 115. The user of the support computer device 175 can communicate with users of the user device 110 via the application 125.

Figure 2:
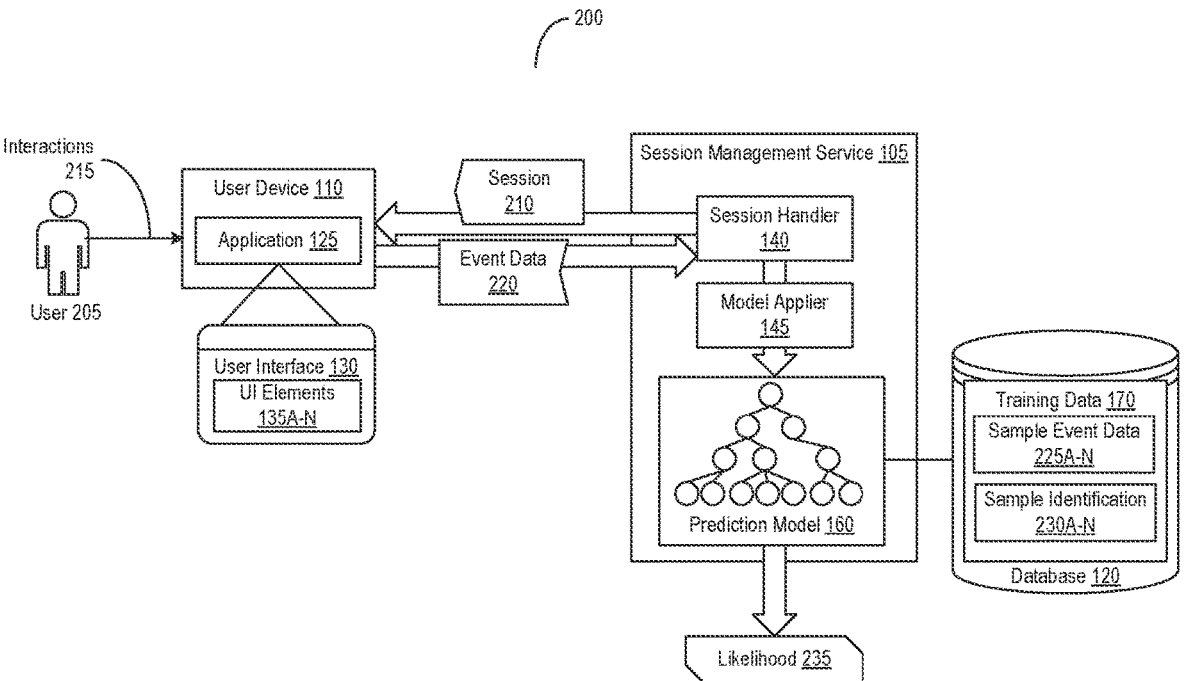
FIG. 2 depicts a block diagram of a process of generating likelihoods of users interacting in subsequent sessions based on event data from prior sessions in the system for detecting expected reductions or persistence of interactions across sessions, in accordance with an illustrative embodiment.

Referring now to FIG. 2, block diagram of a process 200 of generating likelihoods of users interacting in subsequent sessions based on event data from prior sessions in the system 100 for detecting expected reductions or persistence of interactions across sessions. The process 200 may include or correspond to operations performed by the system 100 to generate event data from a session and predict likelihood that the user interacts in a subsequent session. Under process 200, the session handler 140 executing on the session management service 105 may send, transmit, or otherwise provide instructions for at least one session 210 to be presented via the application 125. The instructions may identify or include the digital therapeutic content to be presented via the user interface 130 for the application 125 to a user 205. The instruction may include, for example, a specification as to which UI elements 135 are to be used and may identify content to be displayed on the UI elements 135 of the user interface 130. The instructions may be code, data packets, or a control to present the session to the user 205 via the application 125 running on the user device 110.

For the session 210, the session handler 140 may create, write, or otherwise generate the instruction. In some embodiments, the generation of the instruction may be based on the user profile 165 for the user 205. For example, the session handler 140 may select digital therapeutic content including a lesson based on the medical condition of the user 205 as identified in the user profile 165. In some embodiments, the session handler 140 may generate the instructions for the session 210 to include digital therapeutic content including rhetorical messages to the user 205. For instance, the messages may include informational guides on how to deal with certain medical conditions. In some embodiments, the session handler 140 may generate the instruction for the session 210 to include digital therapeutic content to prompt the user 205 to perform a certain task. The digital therapeutic content may include a set of stimuli (e.g., audio, visual, or text) for the user 205. The task may include, for example, an implicit association task (IAT); an attention bias modification training (ABMT); an emotional faces memory task (EFMT); digital support tool (DST) (sometimes referred herein as a decision support tool); and adaptive goal setting (AGS) among others. The session may correspond to a set number of tasks to be performed by the user 205 within a defined time period. With the generation, the session handler 140 may transmit the instruction for the session 210 to the user device 110.

The application 125 on the user device 110 may retrieve, identify, or otherwise receive the instruction for the session 210. The application 125 may perform, carry out, or otherwise execute the instructions for the session 210. In accordance with the instructions, the application 125 may render, display, or otherwise present the digital therapeutic content via the UI elements 135 of the user interface 130. For example, the user 205 may suffer from high blood pressure and may be recovering from a hand injury. To treat the high blood pressure, the session 210 may include messages directing the user 205 to perform one or more aerobic exercises (e.g., walking, running, or hiking), whereas to treat the hand injury, the user 205 may complete one or more strenuous exercises. The user 205 may interact with the content to treat the high blood pressure as the content is tailored better toward user 205 than the content to treat the hand injury. The content for the high blood pressure may include inspirational quotes, workout music, and various games to play during a time break for the one or more aerobic exercises.

With the presentation of the digital therapeutic content for the session 210, the application 125 on the user device 110 may record, detect, or monitor one or more interactions 215 by the user 205 with the application 125 on the user device 110. Each interaction 215 may correspond to one or more events on the application 125 triggered by the user 205 interacting with the UI elements 135 of the user interface 130, while the session 210 is provided. For example, if the session 210 is for an EFMT, the interactions 215 may include or identify user responses when prompted to indicate whether the first facial expression is the same as the last facial expression. The application 125 may use event listeners or handlers on the UI elements 135 of the user interface 130 to monitor for interactions 215. In some embodiments, the application 125 may use listeners associated with input/output devices on the user device 110 to monitor for interactions 215. For instance, the application 125 may use the camera on the user device 110 to track eye-gaze of the user 205 or inertial sensors on the user device 110 to detect movement or orientation of the user device 110, among others.

Based on the interactions 215, the application 125 may write, create, or otherwise generate event data 220 identifying the interactions 215 by the user 205 with the session 210 for the digital therapeutic content. In some embodiments, the application 125 may generate the event data 220 identifying the interactions 215 over a previous set of sessions (e.g., the previous 3-5 sessions provided to the user 205). The event data 220 may include a log of interactions 215 detected on the UI elements 135 of the user interface 130 presenting the digital therapeutic content and information derived from the set of interactions 215. In some embodiments, the event data 220 may include an identifier of the digital therapeutic content provided in the session 210. For example, the identifier may be a set of alphanumeric characters to reference the individual instance of the session 210, the digital therapeutic content (e.g., lesson, message, or task) provided in the session 210, or number of sessions 210 provided to the user 205, among others.

In some embodiments, the event data 220 may identify or include a time during which the session 210 is provided. The time may identify, for example, a time at which the digital therapeutic content of the session 210 is presented to the user 205, a time at which the instruction for the session 210 is sent to the user device 110, a time at which the digital therapeutic content of the session 210 has finished being presented to the user 205, a time at which the digital therapeutic content of the session 210 has ceased being presented via the user interface 130, among others. In some embodiments, the event data 220 may identify or include a sequence identifier of the session 210 within a set of sessions. The sequence identifier may be used to distinguish between which session 210 the user 205 is currently interacting with. For example, if the user 205 suffers from a speech defect and has received a n sessions to address speech defects, the sequence identifier may be "n" to identify the n-th session.

In some embodiments, the event data 220 may identify or include at least one metric to indicate a degree of interactions 215 with the session 210. The metric may include, for example, a total number of interactions 215, a rate or frequency of interactions 215, a percentage of correct responses to prompts, and an average response time between presentation (e.g., of a stimulus) and a corresponding user interaction by the user 205, among others. The metric may be determined by the application 125 based on the interactions 215. In some embodiments, the event data 220 may identify or include an indication of whether the user 205 contacted the support computer device 175. The indication may be a flag, a binary value, an alphanumeric value, or metadata associated with the event data 220. In some embodiments, the event data 220 may include or identify a device type of the user device 110, such as a smartphone, laptop, desktop, wearable, or smartwatch, among others. In some embodiments, the event data 220 may include a number of prior expected reductions (e.g., determined using the prediction model 160 as detailed herein).

In some embodiments, the event data 220 may identify or include at least one metric associated with the task presented in the digital therapeutic content of the session 210. For example, for the IAB task, the event data 220 may include a response time by the user 205 to the presentation of the stimuli, a rate of correct categorization of stimuli, and a score of associations among stimuli and concepts by the user 205, among others. For the ABMT task, the event data 220 may include a response time by the user 205 to the presentation of each stimuli, a rate of correct responses by the user 205, a rate of incorrect responses by the user 205, a level of attention allocation (e.g., from eye-tracking data), among others. For the EFMT task, the event data 220 may include a response time, a rate of accurate responses, and a level of difficulty (e.g., number of faces between first and last presented facial expression), among others. For the DST task, the event data 220 may identify whether the user 205 performed the specified activity (e.g., behavioral therapies, including cognitive behavioral therapy, biofeedback, and relaxation therapy). In some embodiments, the event data 220 may identify or include at least one metric associated with the condition of the user 205. The metric may identify a level of severity of a symptom of the condition or the condition itself. For instance, the event data 220 may include or identify a pain catastrophizing score (PCS) or number of migraine days over a defined period to measure the level of severity of migraine in the user 205. The score may be gathered through interactions with a prompt presented via the application 125.

The session handler 140 may retrieve, identify, or otherwise receive the event data 220 from the user device 110. With receipt, the session handler 140 may process or parse the event data 220 to extract or identify the log of interactions 215 detected on the UI elements 135 of the user interface 130 presenting the digital therapeutic content and information derived from the set of interactions 215. In some embodiments, the session handler 140 may parse the event data 220 to identify one or more of: the identifier of the digital therapeutic content provided in the session 210; the time during which the session 210 is provided; the sequence identifier; metric to indicate the degree of interactions 215 with the session 210; the indication of whether the user 205 contacted the support computer device 175; the device type; the number of prior expected reductions; the metric associated with the task, or the metric associated with the condition, among others. In some embodiments, the session handler 140 may supplement or add information from the user profile 165 (e.g., maintained on the database 120) to the event data 220. For instance, the session handler 140 may identify the number of prior expected reductions as determined by the prediction model 160 for the user 205.

In conjunction, prior to applying the event data 220 to the prediction model 160, the prediction model 160 may have been initialized, trained, and established (e.g., by the model applier 145 or another device besides the session management service 105) using the training data 170. The model applier 145 (or another device) may initialize, train, or otherwise establish the prediction model 160 using the training data 170. The training data 170 may include a set of examples. For example, the training data 170 may be created from historical data and activity performance by a pool of users. The pool of users may be similar in trait as the user 205, such as in terms of the condition to be addressed, preferences (e.g., preference for types of digital content or messages such as empathetic, exhortatory, or rhetorical), age, or location, among others. Each example may include sample event data 225A-N (hereinafter generally referred to as event data 225) and an associated sample identification 230A-N (hereinafter generally referred to as sample identification 230). The sample event data 225 may identify interactions by a corresponding user with a respective session for digital therapeutic content. The sample event data 225 may include information in a similar form as the event data 220. The sample identification 230 may indicate whether a user interacted in a subsequent session after the session associated with the sample event data 225.

The model applier 145 (or another device) may initialize the set of weights of the prediction model 160 in accordance with the model architecture. Upon initialization, the model applier 145 may commence training of the prediction model 160 in accordance with the learning technique for the model architecture. The model applier 145 may identify the set of examples including the sample event data 225 and the sample identification 230 in the training data 170 to update the weights and architecture of the prediction model 160. For instance, with a random forest as the prediction model 160, the model applier 145 may randomly sample (e.g., via bootstrapping or bagging) examples of the training data 170 to create multiple decision trees for the random forest. At each node, the model applier 145 may determine whether to split the decision tree further via feature selection to de-correlate the decision tree in the random forest of the prediction model 160. The model applier 145 may perform splitting recursively to separate target variables. The model applier 145 may then combine the decision trees to perform ensemble learning. With the completion of ensemble learning, the model applier 145 may use the remaining set of examples in the training data 170 to evaluate the accuracy of prediction, and update the weights of the prediction model 160.

Using the trained prediction model 160, the model applier 145 may input, provide, or apply the event data 220 to the prediction model 160. Based on the feeding or application of the event data 220 to the prediction model 160, the model applier 145 may calculate, determine, or generate at least one likelihood 235 of the user 205 interacting with at least one subsequent session. The likelihood 235 may indicate a value (e.g., a probability) of the user 205 interacting with the session subsequent to the session 210. In some embodiments, the likelihood 235 may be of the user 205 not interacting with the subsequent session. The subsequent session may correspond to a defined time period after the current session 210. To generate, the model applier 145 may feed the event data 220 to the prediction model 160. Upon feeding, the model applier 145 may process the event data 220 in accordance with the weights and model architecture of the prediction model 160. From processing, the model applier 145 may generate the likelihood 235. Different factors may affect or influence the likelihood 235 of the user 205 interacting with the subsequent session. For instance, when the user 205 has contacted the support computer device 175, has shown improvement in terms metrics associated with the condition, or is using a particular type of user device 110, the likelihood 235 of the user 205 interacting with the subsequent session may be higher. Conversely, when the user 205 has not contacted the support computer device 175 or has shown no improvement in the condition, the likelihood 235 of the user 205 interacting with the subsequent session may be lower.

Figure 3:
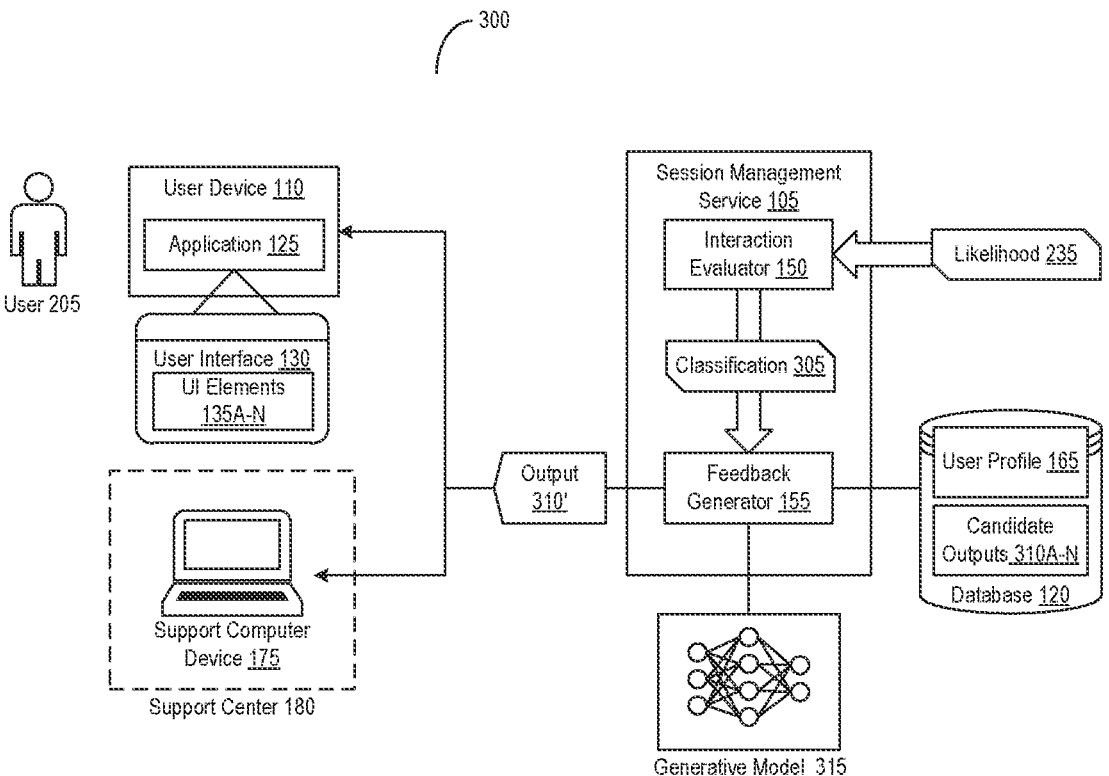
FIG. 3 depicts a block diagram of a process of generating outputs based on likelihoods of users interacting in subsequent session in the system for detecting expected reductions or persistence of interactions across sessions, in accordance with an illustrative embodiment.

Referring now to FIG. 3, depicted is a block diagram of a process 300 of generating outputs based on likelihoods of users interacting in subsequent session in the system 100 for detecting expected reductions or persistence of interactions across sessions. The process 300 may include or correspond to operations performed by the system 100 of generating an output 310 based on the likelihood 235. Under the process 300, the interaction evaluator 150 executing on the session management service 105 may identify or determine at least one classification 305. To determine the classification 305, the interaction evaluator 150 may compare the likelihood 235 with a threshold. The threshold may delineate, identify, or otherwise define a value for the likelihood 235 at which to predict or detect an expected reduction in interaction on the part of the user 205 in the subsequent session. The classification 305 may indicate whether the user is expected to reduce or persist in interactions in the subsequent session.

When the likelihood 235 satisfies (e.g., greater than or equal to) the threshold, the interaction evaluator 150 may identify, predict, determine, or otherwise detect a persistence in user interactions by the user 205 in the next session. The interaction evaluator 150 may determine the classification 305 to indicate the expected (or predicted) persistence. On the other hand, when the likelihood 235 does not satisfy (e.g., less than) the threshold, the interaction evaluator 150 may identify, predict, determine, or otherwise detect an expected reduction in user interactions by the user 205 in the next session. The interaction evaluator 150 may determine the classification 305 to indicate the expected (or predicted) reduction. The interaction evaluator 150 may store and maintain the classification 305 in the database 120. For example, the interaction evaluator 150 may update the user profile 165 for the user 205 with the classification 305. In addition, the interaction evaluator 150 may compare the likelihood 235 to a set of ranges. Each range may correspond to a severity level for the user 205 and may be used to select an appropriate countermeasure to address the expected reduction in user interactions.

The feedback generator 155 executing on the session management service 105 may select or identify at least one of a set of candidate outputs 310A-N (hereinafter generally referred to as candidate outputs 310) based on the likelihood 235 (or the classification 305). The set of candidate outputs 310 may include, for example, one or more of: a first candidate output to indicate to the support computer device 175 to initiate communications via at least one of phone, email, or in-app chat with the user 205; a second candidate output indicating to the support computer device 175 to monitor subsequent interactions by the user 205; a third candidate output to notify (e.g., using a predefined notification) the user 205 to increase engagement with the digital therapeutic; or a fourth candidate output to indicate to the support computer device 175 refraining from initiation of communications or monitoring of the user 205, among others.

Based on the comparison of the likelihood 235 with the set of ranges, the feedback generator 155 may select at least one output 310'. At least some of the candidate outputs may be associated with the set of ranges and by extension a severity level. For example, the first candidate output may be associated with a high-level of severity and may be a high-touch intervention. The second candidate output may be associated with a low-level of severity and may be a low-level intervention. The third candidate output may be associated with intermediate levels of severity and may be a base case intervention. When the likelihood 235 does not satisfy the threshold indicating expected reduction, the feedback generator 155 may select the output 310' from one of the first to third candidate outputs. When the likelihood 235 satisfies the threshold indicating expected persistence, the feedback generator 155 may select the fourth candidate output as the output 310' to indicate to the support computer device 175 refraining from initiation of communications or monitoring of the user 205.

In some embodiments, the feedback generator 155 may write, produce, or otherwise generate the output 310' using at least one generative model 315. The generative model 315 may be a generative transformer model, such as a large language model (LLM) (e.g., ChatGPT or bidirectional encoder representations from transformers (BERT)), among others. The generative model 315 may be hosted on the session management service 105 or on a separate server. To generate, the feedback generator 155 may retrieve, select, or otherwise identify the user profile 165 associated with each user 205, upon detecting the expected reduction. The user profile 165 may identify or include profile information, such as name, condition, preferences, and number of prior expected reductions, among others. The feedback generator 155 may provide, feed, or otherwise apply the profile information to the generative model 315. The generative model 315 may use the profile information to generate a custom notification to direct the user 205 to interact with a subsequent session provided to the user 205. The feedback generator 155 may use the notification generated by the generative model 315 as the output 310'.

With the generation, the feedback generator 155 may transmit, send, or otherwise provide the output 310' for the user 205. In some embodiments, the feedback generator 155 may provide the output 310' to the application 125 of the user device 110. The output 310' provided to the application 125 may include, for example, the predefined notification or the custom notification generated using the generative model 315 to direct the user 205 to interact with the subsequent session. In some embodiments, the feedback generator 155 may transmit the output 310' to the support computer device 175 of the support center 180. For example, the feedback generator 155 may transmit the output 310' to the support computer device 175 to allow the support computer device 175 to initiate communications with the user subsequent to receipt of a notification or start monitoring the interactions by the user 205 with the subsequent session. In some embodiments, the feedback generator 155 may transmit the output 310' to the support computer device 175 to refrain from initiation of communications or monitoring of the user 205, when the classification 305 indicates persistence in interactions.

Figure 4:
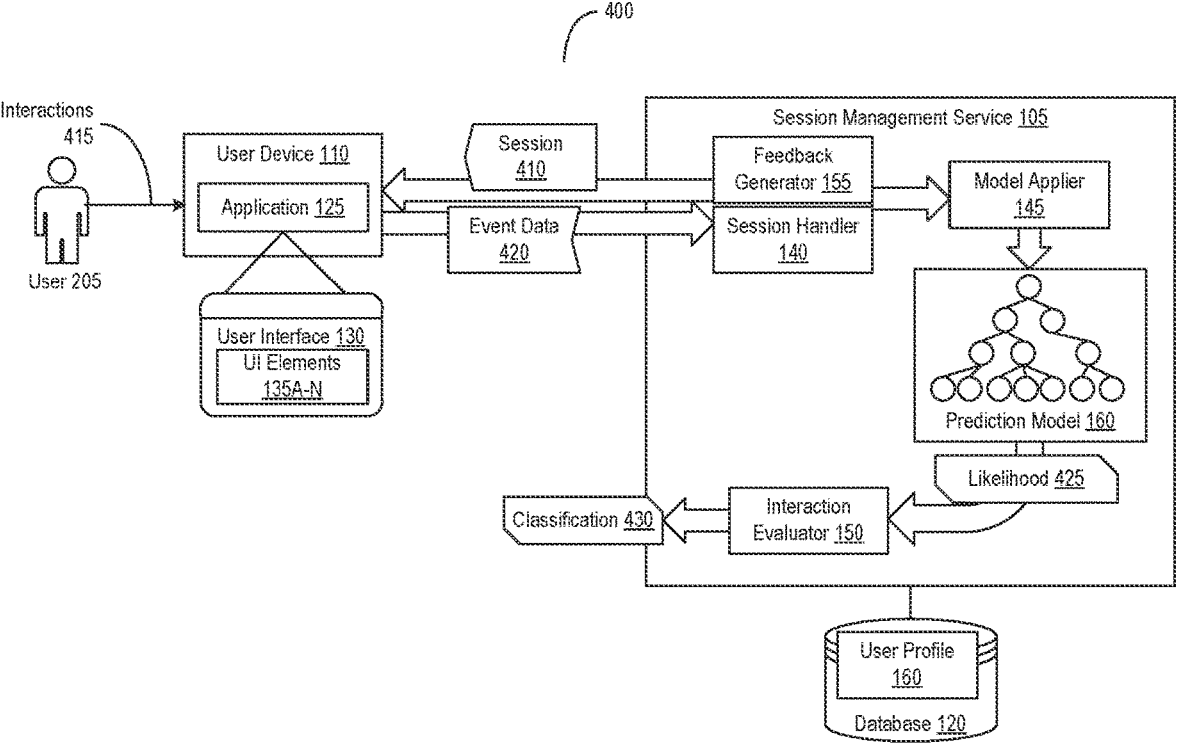
FIG. 4 depicts a block diagram of a process of providing sessions in the system for detecting expected reductions or persistence of interactions across sessions, in accordance with an illustrative embodiment.

Referring now to FIG. 4, depicted is a block diagram of a process 400 of providing sessions in the system 100 for detecting expected reductions or persistence of interactions across sessions. The process 400 may include or correspond to operations performed by the system 100 to provide the subsequent session. Under process 400, the session handler 140 may send, transmit, or otherwise provide instructions for at least one session 410 to be presented via the application 125. The session 410 (also referred to herein as a next or subsequent session) may correspond to a defined time subsequent to the prior session 210. The instructions may identify or include the digital therapeutic content to be presented via the user interface 130 for the application 125 to the user 205. The instruction may include, for example, a specification as to which UI elements 135 are to be used and may identify content to be displayed on the UI elements 135 of the user interface 130. The instructions may be code, data packets, or a control to present the session 410 to the user 205 via the application 125 running on the user device 110.

In some embodiments, the feedback generator 155 may change, alter, or otherwise modify the digital therapeutic content to be presented in the subsequent session 410. The modification of the digital therapeutic content may be performed, when the expected reduction in interactions is detected. The modification may be based on the user profile 165, the likelihood 235, or classification 305, among others. In some embodiments, the feedback generator 155 may identify or select a difficulty level for the digital therapeutic content. For example, the feedback generator 155 may select an easier difficulty level to increase engagement on the part of the user 205. In some embodiments, the feedback generator 155 may identify or select a task for the digital therapeutic content. For instance, the feedback generator 155 may select a different task from the task that the user 205 was previously engaged with. In some embodiments, the feedback generator 155 may select or identify a tone (e.g., empathy, clarity, positivity, trust, respect, exhortation, or personalization) of the messages in the digital therapeutic content. In some embodiments, the feedback generator 155 may change or alter the sequence of digital therapeutic content (e.g., an order of presentation of UI elements 135 on the user interface 130). The feedback generator 155 may provide the modified digital therapeutic as part of the session 410 or the output 310'.

The application 125 on the user device 110 may retrieve, identify, or otherwise receive the instruction for the session 410. The application 125 may perform, carry out, or otherwise execute the instructions for the session 410. In accordance with the instructions, the application 125 may render, display, or otherwise present the digital therapeutic content via the UI elements 135 of the user interface 130. For example, the user 205 may suffer from high blood pressure and recover from a hand injury. To treat the high blood pressure, the session 410 may include messages directing the user 205 to perform one or more aerobic exercises (e.g., walking, running, or hiking), whereas to treat the hand injury, the user 205 may complete one or more strenuous exercises. The user 205 may interact with the content to treat the high blood pressure as the content is tailored better toward user 205 than the content to treat the hand injury. The content for the high blood pressure may include inspirational quotes, workout music, and various games to play during a time break for the one or more aerobic exercises.

With the presentation of the digital therapeutic content for the session 410, the application 125 on the user device 110 may record, detect, or monitor one or more interactions 415 by the user 205 with the application 125 on the user device 110. Each interaction 415 may correspond to one or more events on the application 125 triggered by the user 205 interacting with the UI elements 135 of the user interface 130, while the session 410 is provided. For example, if the session 410 is a go/no-go task, the interactions 415 may include or identify user responses when prompted to indicate whether to respond or not to the presentation of a stimuli. The application 125 may use event listeners or handlers on the UI elements 135 of the user interface 130 to monitor for interactions 415.

Based on the interactions 415, the application 125 may write, create, or otherwise generate event data 420 identifying the interactions 415 by the user 205 with the session 410 for the digital therapeutic content. In some embodiments, the application 125 may generate the event data 420 identifying the interactions 215 over a previous set of sessions (e.g., the previous 3-5 sessions including the session 210 provided to the user 205). The event data 420 may identify or include, for example one or more of: the identifier of the digital therapeutic content provided in the session 410; the time during which the session 410 is provided; the sequence identifier; metric to indicate the degree of interactions 415 with the session 410; the indication of whether the user 205 contacted the support computer device 175; the device type; the number of prior expected reductions, the metric associated with the task presented in the digital therapeutic content, or the metric associated with the condition of the user, among others. In some embodiment, the session handler 140 may supplement or add information from the user profile 165 (e.g., maintained on the database 120) to the event data 420.

The session handler 140 may retrieve, identify, or otherwise receive the event data 420 from the user device 110. With receipt, the session handler 140 may process or parse the event data 420 to extract or identify the log of interactions 415 detected on the UI elements 135 of the user interface 130 presenting the digital therapeutic content and information derived from the set of interactions 415. In some embodiments, the session handler 140 may parse the event data 420 to identify, for example, one or more of: the identifier of the digital therapeutic content provided in the session 410; the time during which the session 410 is provided; the sequence identifier; metric to indicate the degree of interactions 415 with the session 410; the indication of whether the user 205 contacted the support computer device 175; the device type; the number of prior expected reductions; the metric associated with the task presented in the digital therapeutic content; or the metric associated with the condition of the user, among others. In some embodiments, the session handler 140 may supplement or add information from the user profile 165 (e.g., maintained on the database 120) to the event data 420. For instance, session handler 140 may identify the number of prior expected reductions as determined by the prediction model 160 for the user 205.

Using the trained prediction model 160, the model applier 145 may input, provide, or apply the event data 420 to the prediction model 160. Based on the feeding or application of the event data 420 to the prediction model 160, the model applier 145 may calculate, determine, or generate at least one likelihood 425 of the user 205 interacting with a subsequent session. The likelihood 425 may indicate a value (e.g., a probability) of the user 205 interacting with the session subsequent to the session 410. The subsequent session may correspond to a defined time period after the current session 410. To generate, the model applier 145 may feed the event data 420 to the prediction model 160. Upon feeding, the model applier 145 may process the event data 420 in accordance with the weights and model architecture of the prediction model 160. From processing, the model applier 145 may generate the likelihood 125.

The interaction evaluator 150 may identify or determine at least one classification 430. To determine this, the interaction evaluator 150 may compare the likelihood 425 with a threshold. The threshold may delineate, identify, or otherwise define a value for the likelihood 425 at which to detect an expected reduction in interaction on the part of the user 205 in the subsequent session. The classification 430 may indicate whether the user is expected to reduce or persist in interactions in the subsequent session. When the likelihood 425 satisfies (e.g., greater than or equal to) the threshold, the interaction evaluator 150 may identify, determine, or otherwise detect a persistence in user interactions by the user 205 in the next session. The interaction evaluator 150 may determine the classification 430 to indicate the expected persistence.

On the other hand, when the likelihood 425 does not satisfy (e.g., less than) the threshold, the interaction evaluator 150 may identify, determine, or otherwise detect an expected reduction in user interactions by the user 205 in the next session. The interaction evaluator 150 may determine the classification 430 to indicate the expected reduction. The interaction evaluator 150 may store and maintain the classification 430 in the database 120. For example, the interaction evaluator 150 may update the user profile 165 for the user 205 with the classification 430. In addition, the interaction evaluator 150 may compare the likelihood 425 to a set of ranges. Each range may correspond to a severity level for the user 205 and may be used to select an appropriate countermeasure to address the expected reduction in user interactions.

In some embodiments, the interaction evaluator 150 may identify or determine whether a change (e.g., improvement or deterioration) in responsiveness (or interactions) occurs in the user 205 based on a comparison of likelihoods 235 and 425 (or classifications 305 and 430). To compare, the interaction evaluator 150 may calculate or determine a difference in likelihoods 235 and 425. When the difference is negative by at least a threshold margin, the interaction evaluator 150 may determine a decrease (or a deterioration) in responsiveness across the sessions 210 and 410. When the difference is positive by at least the threshold margin, the interaction evaluator 150 may determine an increase (or an improvement) in responsiveness across the sessions 210 and 410. When the difference is within the threshold margin, the interaction evaluator 150 may determine no change in responsiveness.

In some embodiments, the feedback generator 155 may select or identify at least one of a set of candidate outputs 310 based on the change in responsiveness. When there is a decrease (or a deterioration) in responsiveness, the feedback generator 155 may select the first candidate output to indicate to the support computer device 175 to initiate communications with the user 205. When there is no change in responsiveness, the feedback generator 155 may select the second candidate output to the support computer device 175 to monitor subsequent interactions by the user 205. When there is an increase (or an improvement) in responsiveness, the feedback generator 155 may select the third candidate output to notify (e.g., using a predefined notification or custom notification) the user 205 to increase engagement with the digital therapeutic. The feedback generator 155 may also provide output in a similar manner as process 300 described above.

By using event data from prior sessions and a machine learning (ML) model to predict likelihoods of the user interacting with subsequent session provided to the user, the session management service 105 may determine whether to continue with the digital therapeutic sessions or provide more targeted countermeasures (in the form of outputs 310') to improve user adherence. This may allow the session management service 105 and the user device 110 to better and more efficiently allocate computing resources and network bandwidth based on this determination. Other entities, such as the healthcare provider or the administrator of the digital therapeutic, may be able to identify which users to manually intervene (e.g., by initiating communications). From the perspective of the user 205, with the improvement in treatment adherence across multiple sessions, the user 205 may be able to receive the full benefits and effects of the digital therapeutic in addressing the condition of the user 205. When it is determined to provide a more targeted countermeasure to the user 205, the in-person intervention (e.g., initiation of communications) may not only improve the effectiveness of the digital therapeutic delivered to the user 205 but also any medications that the user may be on in concurrence with the digital therapy regimen.

Furthermore, the reliance on prior event data 220 and 420 may resolve the issue with scarcity of data as well as type of contextual factors in accurately and precisely predicting user interactions across sessions. The accurate predictions may allow the session management service 105 and the user device 110 to more efficiently allocate computing resources (e.g., computational power and network bandwidth) in determining whether to continue with digital therapeutic content or provide countermeasures. As a result of providing targeted countermeasures when the user is expected to drop off, the application 125 may increase adherence of the user 205 with the digital therapeutic provided through the sessions, thereby improving the quality of human-computer interactions (HCI) between the user 205 and the application 125.

Figure 5:
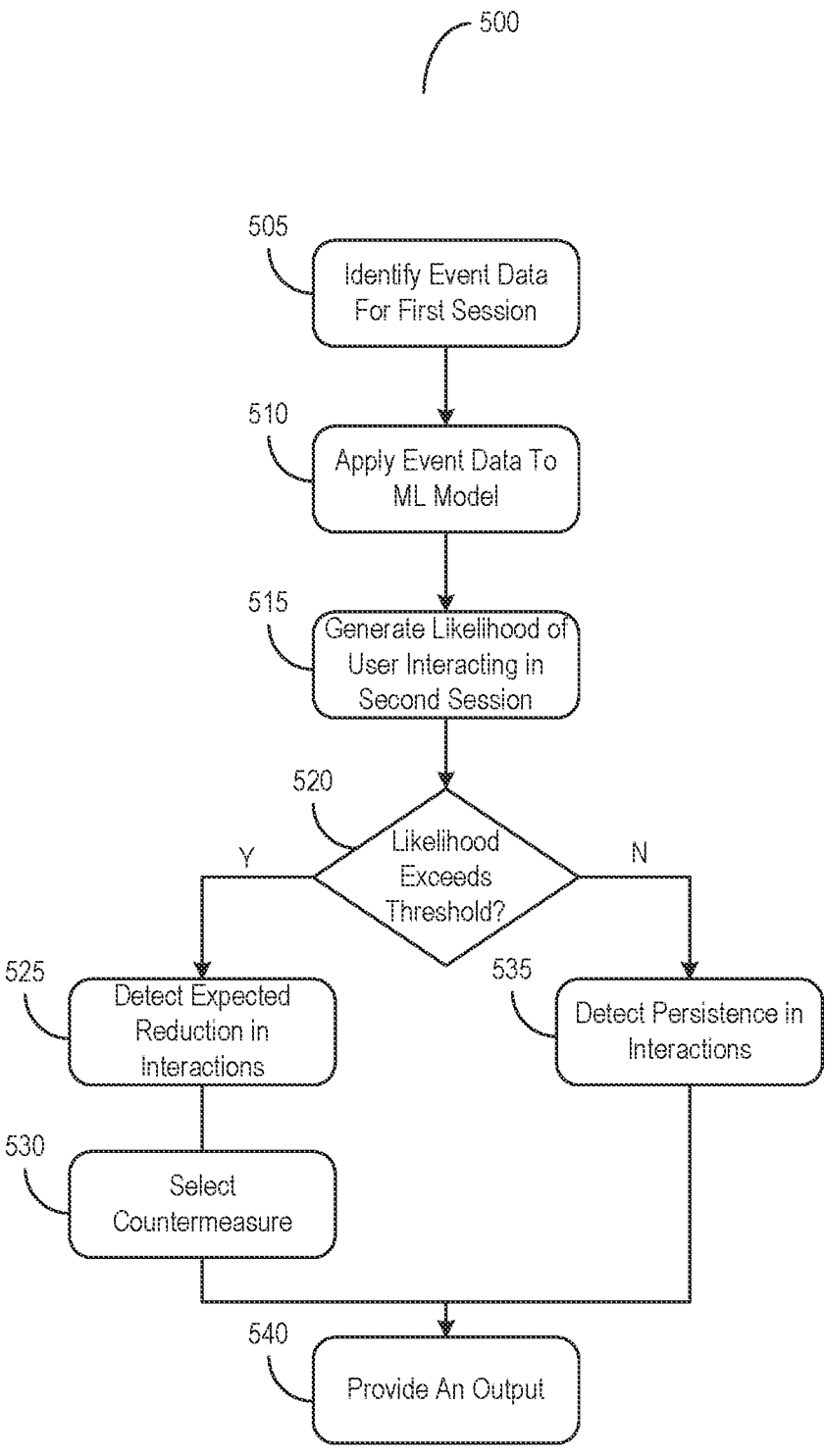
FIG. 5 depicts a flow diagram of a method of the system for detecting expected reductions or persistence of interactions across sessions, in accordance with an illustrative embodiment.

Referring now to FIG. 5, depicted is a flow diagram of a method 500 of providing the output to encourage interactions with the digital therapeutic application. The method 500 may be implemented or performed using any of the components described herein, such as the session management service 105 and the user device 110, or any combination thereof. Under the method 500, a computing system (e.g., the session management service 105 or the user device 110) may identify event data for a first session (505). The computing system may apply the event data to a machine learning (ML) model (e.g., prediction model 160) (510). The computing system may generate a likelihood (e.g., the likelihood 235) of the user interacting with a second session (515). The computing system may determine whether the likelihood exceeds a threshold (520). If the likelihood does not satisfy (e.g., less than) the threshold, the computing system may detect an expected reduction in interactions (525). The computing system may select a countermeasure (e.g., the output 310') to address the expected reduction in interactions (530). If the likelihood does satisfy (e.g., greater than or equal to) the threshold, the computing system may detect persistence in user interactions (535). The computing system may provide an output based on the determination of whether there is the expected reduction or persistence in interactions (540).

Example 1—Use of the Event Prediction Model to Improve Adherence of Digital Therapeutic With ABMT The session handler 140 may provide a session 210 including the digital therapeutic content for ABMT to present to the user 205 to address chronic pain associated with underlying conditions. The application 125 on the user device 110 may gather data associated with the interactions 215 in response to the presentation of the session 210. The session handler 140 may receive event data 220 associated with the ABMT, such as a response time by the user 205 to the presentation of each stimuli, a rate of correct responses by the user 205, a rate of incorrect responses by the user 205, a level of attention allocation (e.g., from eye-tracking data), among others. The model applier 145 may input the event data 220 to the prediction model 160 to generate the likelihood 235 of the user 205 to interact in a subsequent session. Based on the likelihood 235, the interaction evaluator 150 may determine the classification 305 to predict whether the user 205 will interact with the subsequent session. When the classification 305 predicts that the user 205 will likely not interact, the feedback generator 155 may select at least one output 310' to provide to the user 205 to provide an intervention directly to the user and/or to a provider to enable the provider to make an intervention.

By providing sessions 210 and 410 and outputs 310' based on the likelihoods 235 generated by the prediction model 160, a higher rate of returning for subsequent sessions can be achieved and the metric associated with the condition of the user 205 will also show an improvement. For example, by factoring in response time, rate of correct responses, or the level of attention allocation, among other data, it is expected that the prediction model 160 provides more targeted and more accurate likelihoods 235. Furthermore, by providing the outputs 310' based on the likelihoods 235, it will be shown that the user 205 will have a higher rate of interaction with the subsequent sessions. By being exposed to additional sessions 210 and 410 (for ABMT), it is expected that the metrics of the user 205 associated with chronic pain (e.g., pain catastrophizing scale (PCS) values) will show an improvement.

Example 2—Use of the Event Prediction Model to Improve Adherence of Digital Therapeutic With EFMT The session handler 140 may provide a session 210 including the digital therapeutic content for EFMT to present to the user 205 to address affective disorders (e.g., major depressive disorder). The application 125 on the user device 110 may gather data associated with the interactions 215 in response to the presentation of the session 210. The session handler 140 may receive event data 220 associated with the EFMT, such as a response time, a rate of accurate responses, and a level of difficulty (e.g., number of faces between first and last presented facial expression), among others. The model applier 145 may input the event data 220 to the prediction model 160 to generate the likelihood 235 of the user 205 to interact in a subsequent session. Based on the likelihood 235, the interaction evaluator 150 may determine the classification 305 to predict whether the user 205 will interact with the subsequent session. When the classification 305 predicts that the user 205 will likely not interact, the feedback generator 155 may select at least one output 310' to provide to the user 205 to provide an intervention directly to the user and/or to a provider to enable the provider to make an intervention.

By providing sessions 210 and 410 and outputs 310' based on the likelihoods 235 generated by the prediction model 160, a higher rate of returning for subsequent sessions can be achieved and the metric associated with the condition of the user 205 will also show an improvement. For example, by factoring in the response time, the rate of accurate responses, and the level of difficulty, among other data, it is expected that the prediction model 160 provides more targeted and accurate likelihoods 235. Furthermore, from providing the outputs 310' based on the likelihoods 235, it will be shown that the user 205 will have a higher rate of interaction with the subsequent sessions. By being exposed to additional sessions 210 and 410 (for EFMT), it is expected that the metrics of the user 205 associated with affective disorder (e.g., Hamilton Depression Rating Scale (Ham-D)-17 values) will show an improvement.

Example 3—Use of the Event Prediction Model to Improve Adherence of Digital Therapeutic With DST The session handler 140 may provide a session 210 including the digital therapeutic content for DST to present to the user 205 to address migraines. The application 125 on the user device 110 may gather data associated with the interactions 215 in response to the presentation of the session 210. The session handler 140 may receive event data 220 associated with the DST, such as whether the activity as prompted by the digital therapeutic content is performed (e.g., behavioral therapies, including cognitive behavioral therapy, biofeedback, and relaxation therapy), among others. The model applier 145 may input the event data 220 to the prediction model 160 to generate the likelihood 235 of the user 205 to interact in a subsequent session. Based on the likelihood 235, the interaction evaluator 150 may determine the classification 305 to predict whether the user 205 will interact with the subsequent session. When the classification 305 predicts that the user 205 will likely not interact, the feedback generator 155 may select at least one output 310' to provide to the user 205 to provide an intervention directly to the user and/or to a provider to enable the provider to make an intervention.

By providing sessions 210 and 410 and outputs 310' based on the likelihoods 235 generated by the prediction model 160, a higher rate of returning for subsequent sessions can be achieved and the metric associated with the condition of the user 205 will also show an improvement. For example, by factoring in whether the specific activity was performed, among other data, it is expected that the prediction model 160 provides more targeted and more accurate likelihoods 235. Furthermore, by providing the outputs 310' based on the likelihoods 235, it will be shown that the user 205 will have a higher rate of interaction with the subsequent sessions. By being exposed to additional sessions 210 and 410 (for DST), it is expected that the metrics of the user 205 associated with the migraine or disorder (e.g., number of monthly migraine days (MDD) or pain catastrophizing scale (PCS) values) will show an improvement.

B. Network and Computing Environment

Figure 6:
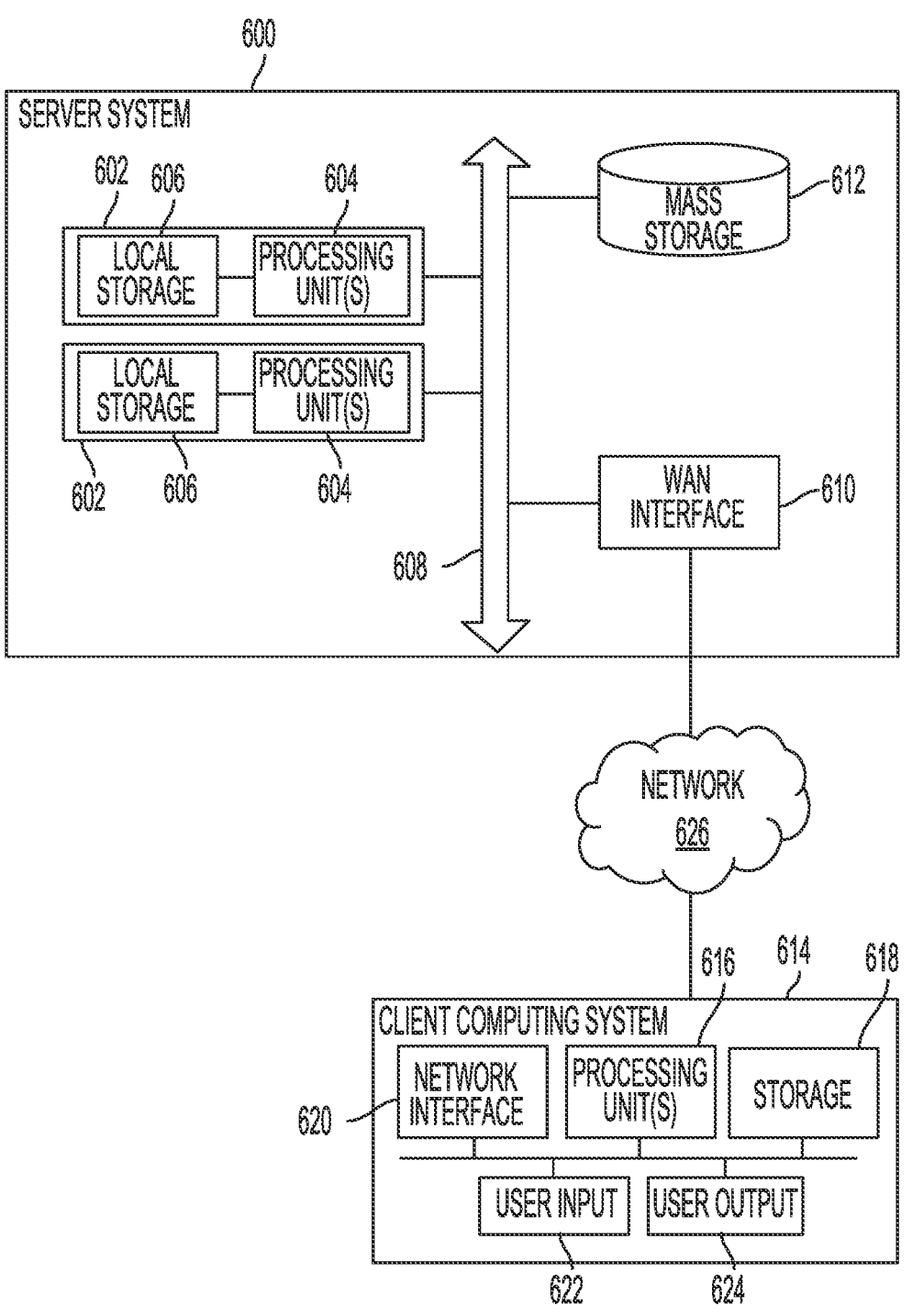
FIG. 6 is a block diagram of a server system and a client computer system in accordance with an illustrative embodiment.

Various operations described herein can be implemented on computer systems. FIG. 6 shows a simplified block diagram of a representative server system 600, client computer system 614, and network 626 usable to implement certain embodiments of the present disclosure. In various embodiments, server system 600 or similar systems can implement services or servers described herein or portions thereof. Client computer system 614 or similar systems can implement clients described herein. The system 100 described herein can be similar to the server system 600. Server system 600 can have a modular design that incorporates a number of modules 602 (e.g., blades in a blade server embodiment); while two modules 602 are shown, any number can be provided. Each module 602 can include processing unit(s) 604 and local storage 606.

Processing unit(s) 604 can include a single processor, which can have one or more cores, or multiple processors. In some embodiments, processing unit(s) 604 can include a general-purpose primary processor as well as one or more special-purpose co-processors such as graphics processors, digital signal processors, or the like. In some embodiments, some or all processing units 604 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 604 can execute instructions stored in local storage 606. Any type of processors in any combination can be included in processing unit(s) 604.

Local storage 606 can include volatile storage media (e.g., DRAM, SRAM, SDRAM, or the like) and/or non-volatile storage media (e.g., magnetic or optical disk, flash memory, or the like). Storage media incorporated in local storage 606 can be fixed, removable, or upgradeable as desired. Local storage 606 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 604 need at runtime. The ROM can store static data and instructions that are needed by processing unit(s) 604. The permanent storage device can be a non-volatile read-and-write memory device that can store instructions and data even when module 602 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 606 can store one or more software programs to be executed by processing unit(s) 604, such as an operating system and/or programs implementing various server functions such as functions of the system 100 or any other system described herein, or any other server(s) associated with system 100 or any other system described herein.

"Software" refers generally to sequences of instructions that, when executed by processing unit(s) 604, cause server system 600 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 604. Software can be implemented as a single program or a collection of separate programs or program modules that interact as desired. From local storage 606 (or non-local storage described below), processing unit(s) 604 can retrieve program instructions to execute and data to process in order to execute various operations described above.

In some server systems 600, multiple modules 602 can be interconnected via a bus or other interconnect 608, forming a local area network that supports communication between modules 602 and other components of server system 600. Interconnect 608 can be implemented using various technologies, including server racks, hubs, routers, etc.

A wide area network (WAN) interface 610 can provide data communication capability between the local area network (e.g., through the interconnect 608) and the network 626, such as the Internet. Other technologies can be used to communicatively couple the server system with the network

626, including wired (e.g., Ethernet, IEEE 802.3 standards) and/or wireless technologies (e.g., Wi-Fi, IEEE 802.11 standards).

In some embodiments, local storage 606 is intended to provide working memory for processing unit(s) 604, providing fast access to programs and/or data to be processed while reducing traffic on interconnect 608. Storage for larger quantities of data can be provided on the local area network by one or more mass storage subsystems 612 that can be connected to interconnect 608. Mass storage subsystem 612 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 612. In some embodiments, additional data storage resources may be accessible via WAN interface 610 (potentially with increased latency).

Server system 600 can operate in response to requests received via WAN interface 610. For example, one of modules 602 can implement a supervisory function and assign discrete tasks to other modules 602 in response to received requests. Work allocation techniques can be used. As requests are processed, results can be returned to the requester via WAN interface 610. Such operation can generally be automated. Further, in some embodiments, WAN interface 610 can connect multiple server systems 600 to each other, providing scalable systems capable of managing high volumes of activity. Other techniques for managing server systems and server farms (collections of server systems that cooperate) can be used, including dynamic resource allocation and reallocation.

Server system 600 can interact with various user-owned or user-operated devices via a wide-area network such as the Internet. An example of a user-operated device is shown in FIG. 6 as client computing system 614. Client computing system 614 can be implemented, for example, as a consumer device such as a smartphone, other mobile phone, tablet computer, wearable computing device (e.g., smart watch, eyeglasses), desktop computer, laptop computer, and so on.

For example, client computing system 614 can communicate via WAN interface 610. Client computing system 614 can include computer components such as processing unit(s) 616, storage device 618, network interface 620, user input device 622, and user output device 624. Client computing system 614 can be a computing device implemented in a variety of form factors, such as a desktop computer, laptop computer, tablet computer, smartphone, other mobile computing device, wearable computing device, or the like.

Processing unit 616 and storage device 618 can be similar to processing unit(s) 604 and local storage 606 described above. Suitable devices can be selected based on the demands to be placed on client computing system 614. For example, client computing system 614 can be implemented as a "thin" client with limited processing capability or as a high-powered computing device. Client computing system 614 can be provisioned with program code executable by processing unit(s) 616 to enable various interactions with server system 600.

Network interface 620 can provide a connection to the network 626, such as a wide area network (e.g., the Internet) to which WAN interface 610 of server system 600 is also connected. In various embodiments, network interface 620 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 622 can include any device (or devices) via which a user can provide signals to client computing system 614; client computing system 614 can interpret the signals as indicative of particular user requests or information. In various embodiments, user input device 622 can include any or all of a keyboard, touch pad, touch screen, mouse or other pointing device, scroll wheel, click wheel, dial, button, switch, keypad, microphone, and so on.

User output device 624 can include any device via which client computing system 614 can provide information to a user. For example, user output device 624 can include display-to-display images generated by or delivered to client computing system 614. The display can incorporate various image generation technologies, e.g., a liquid crystal display (LCD), light-emitting diode (LED) display including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 624 can be provided in addition to or instead of a display. Examples include indicator lights, speakers, tactile "display" devices, printers, and so on.

Some embodiments include electronic components, such as microprocessors, storage, and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 604 and 616 can provide various functionality for server system 600 and client computing system 614, including any of the functionality described herein as being performed by a server or client, or other functionality.

It will be appreciated that server system 600 and client computing system 614 are illustrative and that variations and modifications are possible. Computer systems used in connection with embodiments of the present disclosure can have other capabilities not specifically described here. Further, while server system 600 and client computing system 614 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. Embodiments of the disclosure can be realized using a variety of computer systems and communication technologies, including but not limited to specific examples described herein. Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or digital versatile disk (DVD), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method, comprising:
receiving, by one or more processors, event data identifying interactions by a user with a first session for digital therapeutic content provided to a digital therapeutic application on a user device to address a condition in the user;
training, by the one or more processors, a machine learning (ML) model by:
initializing a plurality of weights of the ML model, using a plurality of examples, each of the plurality of examples including: (i) a respective event data identifying interactions by a corresponding user with a respective session for digital therapeutic content and (ii) a respective identification of whether the corresponding user interacted with a subsequent session after the respective session; and
updating at least one of the plurality of weights using another plurality of examples;
applying, by the one or more processors, the event data to the ML model to generate a likelihood of the user interacting with a second session for digital therapeutic content provided to the digital therapeutic application on the user device to address the condition subsequent to the first session;
determining, by the one or more processors, an expected reduction in interactions by the user with the second session, responsive to the likelihood of the user interacting with the second session not satisfying a threshold;
identifying, by the one or more processors, at least one of (a) a level, placement, timing, or parameter, for at least one portion of the digital therapeutic content provided to the digital therapeutic application on the user device corresponding to the second session or (b) digital therapeutic content to be provided in the second session;
updating, by the one or more processors, user data to indicate the expected reduction in interactions, responsive to determining the expected reduction in interactions corresponding to the likelihood of the user interacting with the second session;
based on (i) the expected reduction and (ii) at least one of the (a) level, placement, timing, or parameter or (b) the digital therapeutic content:
at least one of selecting, modifying, or generating, by the one or more processors, an output to increase interactions during the second session; and
providing, by the one or more processors, the output (i) to the digital therapeutic application on the user device, (ii) to a computing device indicating to initiate communications via at least one of phone, email, or in-app chat, or (iii) to the computing device indicating to monitor subsequent interactions by the user.

2. The method of claim 1, further comprising:
applying, by the one or more processors, event data identifying the interactions by a second user with a third session to the ML model to generate a likelihood of the second user interacting with a fourth session subsequent to the third session;
determining, by the one or more processors, an expected persistence in interactions by the second user with the fourth session, responsive to the likelihood of the second user satisfying the threshold; and
providing, by the one or more processors, an output for the second user, responsive to determining the expected persistence in interactions.

3. The method of claim 1, wherein providing the output further comprises transmitting the output comprising a notification to a computing device of a support center, the computing device configured to initiate communications with the user subsequent to receipt of the notification.

4. The method of claim 1, further comprising selecting, by the one or more processors, the output from a plurality of candidate outputs based on the likelihood of the user interacting with the second session.

5. The method of claim 1, wherein providing the output further comprises transmitting the output comprising a predefined notification to direct the user to interact with the second session to be provided to the user.

6. The method of claim 1, further comprising:
identifying, by the one or more processors, profile information associated with the user, responsive to determining the expected reduction; and
applying, by the one or more processors, the profile information to a generative transformer model to generate a notification to direct the user to interact with the second session to be provided to the user,
wherein providing the output further comprises providing the notification to direct the user to interact with the second session to be provided to the user.

7. The method of claim 1, further comprising modifying, by the one or more processors, the digital therapeutic content to be presented in the second session, responsive to determining the expected reduction, and wherein providing the output further comprises providing the second session for the modified digital therapeutic content to the user.

8. The method of claim 1, further comprising:

identifying, by the one or more processors, second event data identifying interactions by the user with the second session for digital therapeutic content to address the condition;

applying, by the one or more processors, the second event data to the ML model to generate a likelihood of the user interacting with a third session for digital therapeutic content to address the condition subsequent to the second session; and determining, by the one or more processors, whether a change in responsiveness occurs in the user, based on a comparison of the likelihood of the user interacting with the second session and the likelihood of the user interacting with the third session.

9. The method of claim 1, wherein the event data further comprises at least one of: (i) an identifier of the digital therapeutic content provided in the first session, (ii) a time during which the first session is provided, (iii) a sequence identifier of the first session within a plurality of sessions, (iv) a metric indicating a degree of interactions in the first session, (v) an indication of whether the user contacted a computing device for support, (vi) a type of a user device associated with the user, (vii) a number of prior expected reductions, (ix) a metric associated with a task performed in the first session, or (x) a metric associated with the condition.

10. The method of claim 1, wherein the user is on a medication to address the condition, in at least partial concurrence with at least one of the first session or the second session.

11. A system, comprising:

one or more processors coupled with memory, configured to:

receive event data identifying interactions by a user with a first session for digital therapeutic content provided to a digital therapeutic application on a user device to address a condition in the user;

train a machine learning (ML) model by:

initializing a plurality of weights of the ML model, using a plurality of examples, each of the plurality of examples including: (i) a respective event data identifying interactions by a corresponding user with a respective session for digital therapeutic content and (ii) a respective identification of whether the corresponding user interacted with a subsequent session after the respective session; and updating at least one of the plurality of weights using another plurality of examples;

apply the event data to the ML model to generate a likelihood of the user interacting with a second session for digital therapeutic content provided to the digital therapeutic application on the user device to address the condition subsequent to the first session;

determine an expected reduction in interactions by the user with the second session, responsive to the likelihood of the user interacting with the second session not satisfying a threshold;

identify at least one of (a) a level, placement, timing, or parameter, for at least one portion of the digital therapeutic content provided to the digital therapeutic application on the user device corresponding to the second session or (b) digital therapeutic content to be provided in the second session;

update user data to indicate the expected reduction in interactions, responsive to determining the expected reduction in interactions corresponding to the likelihood of the user interacting with the second session;

based on (i) the expected reduction and (ii) at least one of the (a) level, placement, timing, or parameter or (b) the digital therapeutic content:

at least one of select, modify, or generate, an output to increase interactions during the second session; and provide, to the digital therapeutic application, the output (i) to the digital therapeutic application on the user device, (ii) to a computing device indicating to initiate communications via at least one of phone, email, or in-app chat, or (iii) to the computing device indicating to monitor subsequent interactions by the user.

12. The system of claim 11, wherein the one or more processors are configured to:

apply event data identifying the interactions by a second user with a third session to the ML model to generate a likelihood of the second user interacting with a fourth session subsequent to the third session for the second user;

determine an expected persistence in interactions by the second user with the fourth session, responsive to the likelihood of the second user satisfying the threshold; and provide an output for the second user, responsive to determining the expected persistence in interactions.

13. The system of claim 11, wherein the one or more processors are configured to transmit the output comprising a notification to a computing device of a support center, the computing device configured to initiate communications with the user subsequent to receipt of the notification.

14. The system of claim 11, wherein the one or more processors are configured to select the output from a plurality of candidate outputs based on the likelihood of the user interacting with the second session.

15. The system of claim 11, wherein the one or more processors are configured to transmit the output comprising a predefined notification to direct the user to interact with the second session to be provided to the user.

16. The system of claim 11, wherein the one or more processors are configured to:

identify profile information associated with the user, responsive to determining the expected reduction;

apply the profile information to a generative transformer model to generate a notification to direct the user to interact with the second session to be provided to the user; and provide the notification to direct the user to interact with the second session to be provided to the user.

17. The system of claim 11, wherein the one or more processors are configured to:

modify the digital therapeutic content to be presented in the second session, responsive to determining the expected reduction, and wherein providing the output the one or more processors are further configured to provide the second session for the modified digital therapeutic content to the user.

18. The system of claim 11, wherein the one or more processors are configured to:

identify second event data identifying interactions by the user with the second session for digital therapeutic content to address the condition;

apply the second event data to the ML model to generate a likelihood of the user interacting with a third session for digital therapeutic content to address the condition subsequent to the second session; and determine whether a change in responsiveness occurs in the user, based on a comparison of the likelihood of the user interacting with the second session and the likelihood of the user interacting with the third session.

19. The system of claim 11, wherein the event data further comprises at least one of: (i) an identifier of the digital therapeutic content provided in the first session, (ii) a time during which the first session is provided, (iii) a sequence identifier of the first session within a plurality of sessions, (iv) a metric indicating a degree of interactions in the first session, (v) an indication of whether the user contacted a computing device for support, (vi) a type of a user device associated with the user, (vii) a number of prior expected reductions, (ix) a metric associated with a task performed in the first session, or (x) a metric associated with the condition.

20. The system of claim 11, wherein the user is on a medication to address the condition, in at least partial concurrence with at least one of the first session or the second session.

\*   \*   \*   \*   \*